United States Patent

Plant Pat. 3,801
Patented Nov. 11, 1975

3,801

JUNIPER BAKAUREA

John Cornelius Bakker, Jr., St. Catharines, Ontario, Canada, assignor to J. C. Bakker & Sons Ltd., St. Catharines, Ontario, Canada Filed Jan. 17, 1974, Ser. No. 434,035
Int. Cl. A01h 7/00
U.S. Cl. Plt.—50 1 Claim

ABSTRACT OF THE DISCLOSURE

A juniper plant which was discovered and selected from among unpatented varieties known as Juniperus × media *pfitzeriana aurea.*

SUMMARY OF THE INVENTION

My invention relates to a new and distinct variety of Juniperus which was discovered by me among plants of the unpatented variety known as Juniperus × media *pfitzeriana aurea,* said discovery having been made by me in April 1961.

At the time of the discovery, I was planting a quantity of small Juniperus × media *pfitzeriana aurea* when I noted one plant different from all the others. The one plant was identified and observed by me regularly through 1961 and 1962. By the summer of 1962, the difference between this one plant and all others in the field had become more pronounced and distinct. In September 1963, this one plant was singled out as something special for propagation. Cuttings were taken in 1963 and subsequently for nine seasons. The characteristics which I observed and which distinguish my new juniper from all others are established and hold true as shown through asexual reproduction by cuttings as performed at St. Catharines, Ontario, Canada, and at West Grove, Pa., United States of America.

My discovery differs from Juniperus × media *pfitzeriana aurea* by having more pronounced gold color throughout the plant; it is more dense; it does not grow as high; the plant foliage is all of the juvenile form. The foliage is all juvenile foliage except for developing shoots which have scale-like leaves. It has a more compact habit of growth. My discovery differs from the variety known as Juniperus × media "Old Gold" by having more vigorous growth and by having foliage of the juvenile form. My discovery differs from the variety according to Plant Pat. No. 2,491 by the golden color being more vivid and not limited to the tips of the branches. My discovery further differs from the variety known as Juniperus × media "Gold Coast" (Plant Pat. No. 2,491) by having all of its foliage of the juvenile form.

BRIEF DESCRIPTION OF DRAWINGS

The accompanying drawings show typical specimens of the vegetative growth of my new discovery in different stages of development and as depicted in color as nearly true as possible to make them in a color illustration of this nature.

DETAILED DESCRIPTION OF DISCLOSURE

Figure 1:
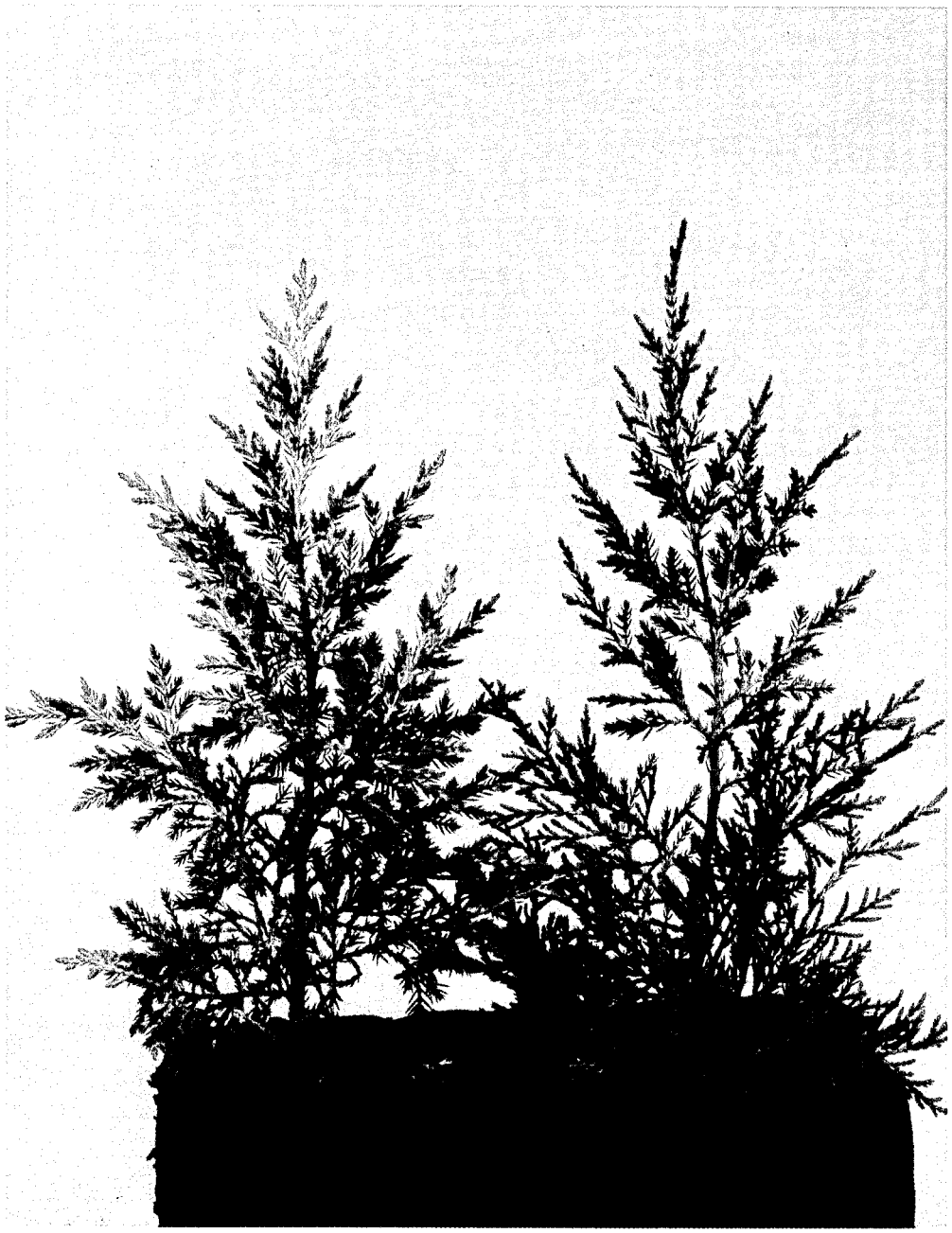
FIG. 1 is a view of typical specimens of the plant.
Figure 2:
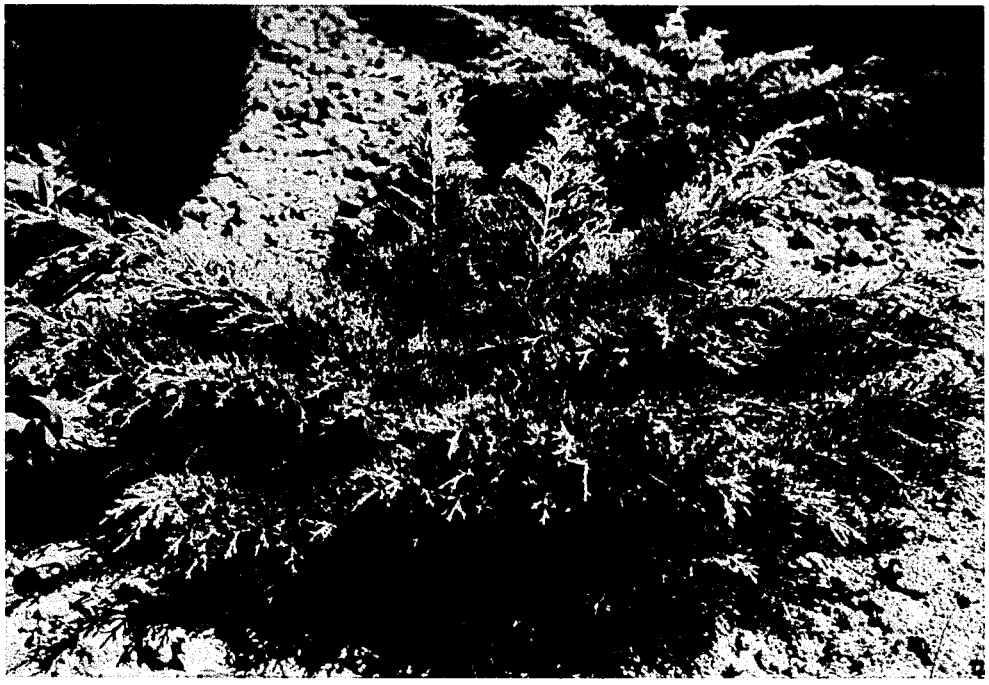
FIG. 2 is a view of the plant in summer color.
Figure 3:
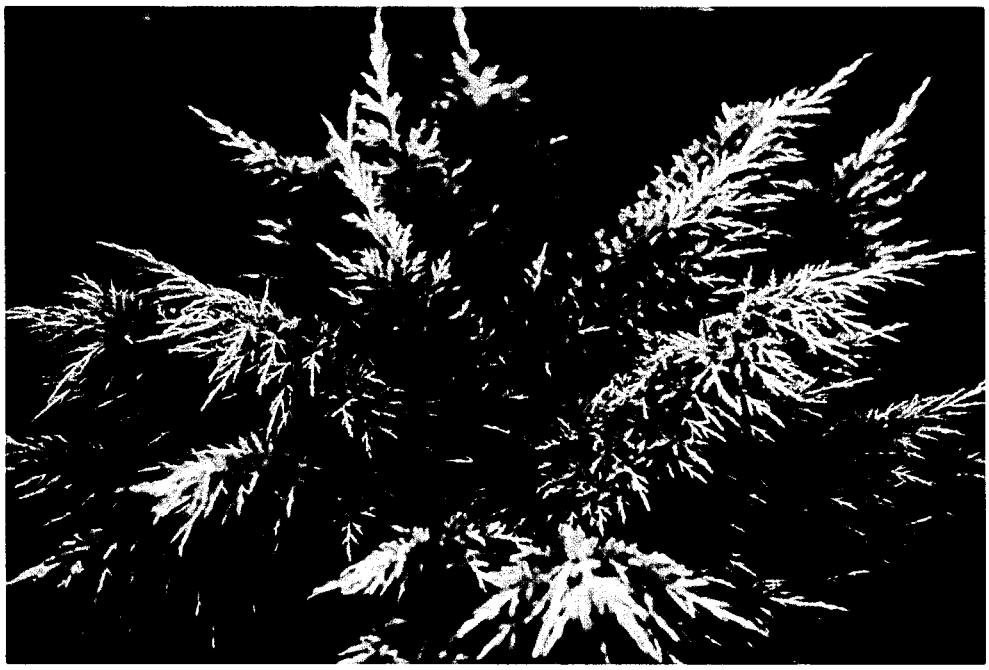
FIG. 3 is a similar view of the plant in winter color.

The following description was made Aug. 29, 1973, from plants growing in full sun at West Grove, Pa. Color designations are the Royal Horticultural Society Colour Chart, except where general color terms are used.

Foliage:

*Type.*—Juvenile, needle shaped.

*Summer color.*—New leaves at the growing tip of primary and secondary branches 138B on upper side of growing tip. On the lower side of the growing tip, the leaves are 154B at the point of attachment, becoming 143C at the tip of the leaf. New leaves unfolding from the upper side of the branch have the general color effect 143A. On the underside of the branch, leaves are 151C at point of attachment and through the center of the leaf where it becomes 144A.

*Winter color.*—Leaves at the tips of primary and secondary branches where exposed to weather 177B on upper side and 165B on the lower side. Foliage on the outside of the plant where exposed to weather has the general color effect of 177A. Foliage on the lower side of the branch on the outside of the plant where protected from weather has the general color effect of 152B. Leaves on the inside of the plant where protected from weather on the upper side of the branch 137C becoming 145B at the point of attachment, 137C on the underside of the branch. Foliage has the general color effect of 147B. Mature foliage has the general color effect of 137C.

Branches:

*Summer color.*—The growing tip of main branches and side shoots of main branches are 3C becoming 154C. As the branches and shoots mature, they become 177D progressing through 177C, 177B and with mature wood 177A. Secondary branches are 160B where protected from the weather, and 162B where exposed to the weather. General color effect of leaves on stems at ends of main branches is 138B on the upper surface and 146C on the lower surface.

*Winter color.*—Outer branches 15C on the upper side becoming 165B and then 175A as the branches and shoots mature. On the under side 25C becoming 165B and then 175A as the branches and shoots mature.

GENERAL OBSERVATIONS

The original plant I discovered has been observed continuously since I first noticed it. In 1973, it has a spread of over 6 feet and is approximately eighteen inches high. The winter hardiness has been proven with no injury in St. Catharines, Ontario, Canada, where the low temperature has been 10° below zero Fahrenheit, with a windchill factor of −35° Fahrenheit.

The golden color is most vivid and covers the plant most when grown in full sun. As direct sunlight is decreased, the gold color decreases and may disappear from plants grown in full shade.

Propagation of my new juniper is readily accomplished through hardwood cuttings in winter or cuttings of new growth placed under mist in summer. The new plants from cuttings grow vigorously with few problems from insect or disease pests resulting in few losses among growing plants.

My new juniper lends itself to accepted production methods, techniques and cultural practices of field-grown nursery stock and appears to be well adapted to container production of nursery stock in a variety of soils as well as soilless composts.

Plants growing in the nursery and in landscape plantings have dense, compact growth requiring less pruning and shaping than customary for similar junipers.

When viewed from above, the branching structure of my new juniper often has a star form.

I claim:

1. A new and distinct variety of juniper plant, substantially as herein shown and described, characterized particularly as to novelty by a unique combination of vigorous, dense and compact growth, low growing and spreading growth habit with attractive foliage of juvenile form, not being lacy; and with branches of golden color which is pronounced and vivid over the plant and is not confined principally to the growing tips.

No references cited.

ROBERT E. BAGWILL, Primary Examiner